United States Patent [19]

Bultman et al.

[11] 4,012,529
[45] Mar. 15, 1977

[54] CONTROL OF MARINE BORER ATTACK ON WOOD

[75] Inventors: John Dale Bultman, Washington, D.C.; Leonard Jurd, Berkeley, Calif.; Ruth D. Turner, Cambridge, Mass.

[73] Assignee: The United States of America as represented by the Secretary of Agriculture, Washington, D.C.

[22] Filed: Mar. 15, 1976

[21] Appl. No.: 667,056

[52] U.S. Cl. .................................. 424/331; 21/7; 21/58; 260/396 N; 424/346
[51] Int. Cl.$^2$ .................. A01N 9/02; A01N 9/26; A61L 13/00; B27K 3/38
[58] Field of Search ........... 21/7, 58; 424/346, 331; 260/396 N; 427/440

[56] References Cited

UNITED STATES PATENTS 3,925,558  12/1975  Bultman et al. ............... 424/331
3,951,820  4/1976  Jurd et al. ...................... 21/58

OTHER PUBLICATIONS

Jurd et al.; "Phenolic & Quinoidal Constituents . . ."; 1972; pp. 2149–2152; Tetrahedron Letters; No. 21.

*Primary Examiner*—Morris O. Wolk
*Assistant Examiner*—Bradley R. Garris
*Attorney, Agent, or Firm*—M. Howard Silverstein; David G. McConnell

[57]  ABSTRACT

Substances, particularly wood, which are normally subject to deterioration due to marine borers are preserved by applying to the substance certain 4-(3-phenylpropenylidene)-2,5-cyclohexadieneones substituted at position 5 with substituents selected from the group consisting of lower alkyl, lower alkoxy, and hydrogen, and at position 2 with substituents selected from the group consisting of hydroxyl and lower alkoxyl.

8 Claims, No Drawings

CONTROL OF MARINE BORER ATTACK ON WOOD

DESCRIPTION OF THE INVENTION

This invention relates to the preservation of substances which are normally subject to deterioration due to marine boring organisms. The objects of the invention include the provision of novel processes and compositions for such preservation. Further objects of the invention will be evident from the following description wherein parts and percentages are by weight unless otherwise specified. Temperatures are given in degrees Centigrade. The symbol $\phi$ is used to designate the phenyl radical.

Many substances, particularly wood, are used in a marine environment, i.e., they are immersed in water for extended periods of time. One problem is that these substances are susceptible to attack and subsequent deterioration and destruction by marine boring organisms found in most bodies of water. Heretofore, such substances have been treated with whole creosote or a mixture of coal tar and creosote to preserve them. While this treatment prevents attack by marine borers for a period of time, even creosoted timbers are destroyed in a few years. Apparently, the constituents within creosote, which are toxic to marine borers, are leached from impregnated timbers and pilings into the surrounding water over a period of time. Consequently, the treated timbers eventually lose their resistance and become susceptible to damage by borer species from which they were originally protected. Repair and replacement is costly, running into many millions of dollars each year. In addition, the toxic components which are extracted into the water contribute to pollution of the environment. The future of creosote as a protectant is uncertain, not only because of its polluting tendencies, but also because it contains carcinogenic materials which are also leached out by the water.

Other preservative treatments are known but they are either not persistent or are undesirable for environmental reasons.

The invention described herein provides a means for obviating the above problems. In accordance with the invention, wood susceptible to deterioration due to marine borers can be preserved indefinitely by applying certain agents thereto prior to immersion in water.

The agents in question have the structure

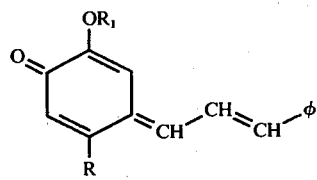

wherein R is lower alkyl, lower alkoxy, or hydrogen and $R_1$ is lower alkyl or hydrogen. "Lower" alkyl and "lower" alkoxy are defined herein as containing 1–4 carbon atoms.

The compounds of the invention are especially useful because they are active against many types of marine borers, particularly against teredine marine borers, i.e., molluscan borers of the family, Teredinidae. The instant compounds have the advantage of being extremely insoluble in water; thus, they are not leached from the wood treated therewith. Further, because the compounds of the invention are persistent, pollution of water in which they are immersed is prevented.

In preventing attack and deterioration of wood by marine borers, the compounds of the invention act as marine borer larvicides. The larvae penetrate the surface of the wood and ingest molecules of the instant compounds within the wood tissues. As a result the larvae die. In this respect it should be noted that once marine borer larvae gain entrance into the wood they metamorphose into adult borers which remain in the wood throughout their lifetime. If the larvae are not killed and eventually become adults, they continuously enlarge their burrows to accommodate new growth, thus systematically destroying the wood. Since it is the larvae which enter the wood and since it is the larvae which advance to adult borers, the compounds of the invention offer an important method for controlling marine borer populations as well as preserving wood treated therewith.

Examples of particular compounds within the scope of the invention are given below by way of illustration and not limitation:

4-(3-phenylpropenylidene)-2-hydroxy-5-methyl-2,5-cyclohexadieneone 4-(3-phenylpropenylidene)-2-hydroxy-5-ethyl-2,5-cyclohexadieneone 4-(3-phenylpropenylidene)-2-hydroxy-5-propyl-2,5-cyclohexadieneone 4-(3-phenylpropenylidene)-2-hydroxy-5-butyl-2,5-cyclohexadieneone 4-(3-phenylpropenylidene)-2-hydoxy-5-isopropyl-2,5-cyclohexadieneone 4-(3-phenylpropenylidene)-2-hydroxy-5-isobutyl-2,5-cyclohexadieneone 4-(3-phenylpropenylidene)-2-hydroxy-5-t-butyl-2,5-cyclohexadieneone 4-(3-phenylpropenylidene)-2-hydroxy-5-methoxy-2,5-cyclohexadieneone 4-(3-phenylpropenylidene)-2-hydroxy-5-ethoxy-2,5-cyclohexadieneone 4-(3-phenylpropenylidene)-2-hydroxy-5-propoxy-2,5-cyclohexadieneone 4-(3-phenylpropenylidene)-2-hydroxy-5-butoxy-2,5-cyclohexadieneone 4-(3-phenylpropenylidene)-2-methoxy-5-methyl-2,5-cyclohexadieneone 4-(3-phenylpropenylidene)-2,5-dimethoxy-2,5-cyclohexadieneone The invention encompasses not only the use of the above-described agents individually but also mixtures thereof.

Furthermore, it is within the compass of the invention to use any of the above-named agents mixed in approximately equal proportions with the compound—4-(3-phenyl-2-propenyl)phenol—represented by the following formula:

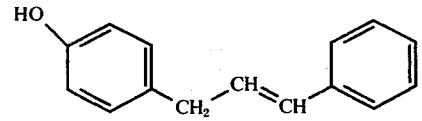

We have discovered that such a mixture exhibits a synergistic effect, i.e., one above any additive effect which might be expected. It is important to note that 4-(3-phenyl-2-propenyl)-phenol alone exhibits little, if any, preservative effects against marine-boring organisms when applied to wood.

In protecting substances in accordance with the invention any of the aforesaid agents or mixtures thereof are applied to the substance, using an amount of the agent which will protect the substance from deterioration, i.e., decomposition and destruction due to marine borers, when immersed in water. Generally, this amount is directly related to the amount necessary to kill the marine borer larvae.

For best results the wood to be protected is impregnated with any of the aforesaid agents or mixtures thereof. A solution of an agent of the invention in a suitable organic solvent is prepared and the wood is immersed therein, whereby the agent of the invention is absorbed within the wood fibers. Organic solvents which may be used to form solutions with the agents of the invention include, but are not limited to, acetone, ethyl ether, ethanol, benzene, xylene, etc.

Impregnation of the wood may be accomplished by employing any conventional wood-treating technique or facility. For example, a Bethel full-cell, vacuum/pressure technique affords an efficient means of impregnating wood with any of the above-mentioned agents.

The invention is of wide versatility and can be used for the preservation of all kinds of substances which are normally subject to deterioration due to marine borer larvae. Typical examples of such substances are listed below by way of illustration and not limitation and include softwoods and hardwoods such as cedar, ash, fir, basswood or linden, beech, birch, butternut, cottonwood or poplar, dogwood, elm, gum tree or sweet gum, hemlock, hickory, chestnut, locust, maple, oak, pine, sassafras, spruce, sycamore or buttonwood, tulip, tupelo or sour gum, walnut, redwood, larches, cypress, alder, mahogany, cherry, and the like.

As mentioned earlier, the compounds of the invention are effective in preserving substances, particularly wood, which are normally subject to deterioration due to marine borers. The agents are particularly effective against teredine marine borers, including *Lyrodus pedi-*
*cellatus*, *Teredo navalis*, *T. bartschi*, *Bankia gouldi*, *B. zetecki*, and the like.

It is within the compass of the invention to employ the instant agents with other wood preservatives. Thus, a compound of the invention or mixtures of such compounds may be incorporated with other agents which preserve wood against microorganisms, other marine organisms, etc. The resulting mixture would then be applied to the wood to be protected.

The compounds of the invention may be synthesized by known procedures. The following scheme outlines a typical synthetic plan, the preparation of 4-(3-phenylpropenylidene)-2-hydroxy-5-methyl-2,5-cyclohexadieneone being selected for purpose of illustration:

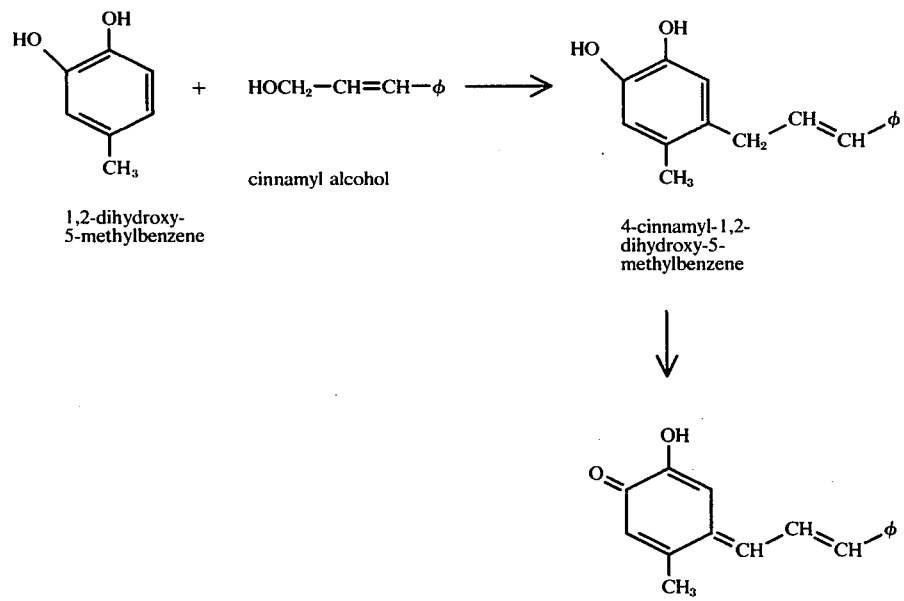

In the initial reaction cinnamyl alcohol is condensed with an appropriately substituted dihydroxybenzene—in this particular example, 1,2-dihydroxy-5-methylbenzene—under acidic conditions to produce the intermediate 4-cinnamyl-1,2-dihydroxy-5-methylbenzene. The latter compound is then oxidized to yield the desired product. Any suitable conventional oxidation method may be employed, but it is preferred to oxidize the intermediate with 2,3-dichloro-5,6-dicyano-1,4-benzoquinone (DDQ) in boiling benzene. Typically, 10–20 grams of the intermediate is dissolved in 50 to 100 milliliters of warm benzene and this solution is added to 16–22 grams of DDQ in 150–200 milliliters of boiling benzene. The mixture is refluxed for a period of 5–10 minutes, during which time the desired product is formed.

EXAMPLES

The invention is further demonstrated by the following illustrative examples.

EXAMPLE 1

Preparation of 4-(3-Phenylpropenylidene)-2-hydroxy-5-methyl-2,5-cyclohexadieneone A mixture of 1,2-dihydroxy-5-methylbenzene (124 g.) and cinnamyl alcohol (134 g.) in 2% aqueous citric acid (1.5 l.) containing ascorbic acid (10.0 g.) was boiled at reflux for 20 hours. After cooling, an oily layer separated and was collected and distilled to give 4-cinnamyl-5-methyl-1,2-dihydroxybenzene (119 g.) as a colorless oil, b.p. 205°–230° at 1.0 mm Hg. The oil was crystallized from a benzene/low-boiling petroleum ether (1/1) mixture to give colorless needles, m.p. 85°. Found: C, 79.9; H, 6.68. Calculated for $C_{16}H_{16}O_2$: C, 80.0; H, 6.71. The 100 MHz nuclear magnetic resonance (nmr) spectrum of this compound in deuterated chloroform exhibited a singlet (3 protons) at δ 2.07, a doublet (2 protons) at δ 3.37 (J = coupling constant = 5.0 Hz), a singlet (2 protons) at δ 5.02, a multiplet (2 protons) at δ 6.23–6.31, a singlet (1 proton) at δ 6.65, a singlet (1 proton) at δ 6.68, and a multiplet (5 protons) at δ 7.10–7.38.

A solution of the above-prepared compound (12.0 g.) in warm benzene (50 ml.) was added to a solution of DDQ (16.0 g.) in boiling benzene (150 ml.). The mixture was refluxed for 5 minutes. The warm mixture as filtered and the filtrate was treated with low-boiling petroleum ether (30 ml.). On cooling, the product crystallized (8.6 g.) and was recrystallized from benzene to give 4-(3-phenylpropenylidene)-2-hydroxy-5-methyl-2,5-cyclohexadieneone as orange-colored needles, m.p. 164°–165°. Found: C, 80.4; H, 5.95. Calculated for $C_{16}H_{14}O_2$: C, 80.6; H, 5.92. The 100 MHz nmr spectrum is deuterated chloroform exhibited a doublet (3 protons) at δ 2.32 (J = 1.0 Hz), a singlet (1 proton) at δ 6.41, and a multiplet (10 protons) at δ 6.86–7.60.

EXAMPLE 2

Preservation of Pine under Laboratory Conditions

Acetone solutions (3%, weight/volume) of the compounds to be tested were used to treat white pine sapwood discs (¼ inch × 2 inches diameter). The discs were dried prior to treatment by solvent extraction according to known procedures. Impregnation of the pine discs was accomplished, using a modified Bethel full-cell treating process. The device used to treat the wood comprised a pressure/vacuum chamber and an externally connected reservoir to contain the impregnating solution. Nitrogen was applied under pressure to force the solution into the wood. Routinely, the vacuum and pressure cycles were maintained for 1 hour, the latter at 100 psig of the gas. At the conclusion of the treatment, each pre-weighed disc was wiped of excess solvent and weighed again to determine the amount of solution absorbed by the wood. Tests indicated that the solvent and solute was uniformly distributed throughout the wood. Excess solvent was removed by placing the discs in a vacuum dessicator at 40° for 1 hour intervals until the wood no longer lost weight.

Treated discs were exposed to a laboratory colony of the teredine borer, *Lyrodus pedicellatus*, for a period of 16 months. Compounds used as preservatives were:

| Run | Compound |
|---|---|
| A | 4-(3-phenylpropenylidene)-2-hydroxy-5-methyl-2,5-cyclohexadieneone [PC-2-OH-5-CH₃] |
| B | 4-(3-phenylpropenylidene)-2-hydroxy-5-methoxy-2,5-cyclohexadieneone [PC-2-OH-5-OCH₃] |
| C | 4-(3-phenylpropenylidene)-2,5-dimethoxy-2,5-cyclohexadieneone [PC-2-OCH₃-5-OCH₃] |
| D | 1:1 mixture of PC-2-OH-5-OCH₃:4-(3-phenyl-2-propenyl)phenol [PP] |

The abbreviations employed above may be explained as follows (with reference to Run A): PC refers to the base structure 4-(3-phenylpropenylidene)-2,5-cyclohexadieneone. The hydroxyl substituent at position 2 is designated "—2—OH" and the methyl substituent at position 5 is designated "5—CH₃." The result is the shortened expression PC—2—OH—5—CH₃ for the compound 4-(3-phenylpropenylidene)-2-hydroxy-5-methyl-2,5-cyclohexadieneone.

The compounds employed in Runs B and C, namely PC—2—OH—5—OCH₃ and PC—2—OCH₃—5—OCH₃, were prepared by procedures analogous to that described in Example 1 for PC—2—OH—5—CH₃. Of course, the appropriate starting phenol was selected for the cinnamylation.

The compound employed in the mixture with PC—2—OH—5—OCH 3 in Run D, namely, PP, was prepared in accordance with the procedure outlined by L. Jurd in *Tetrahedron Letters* No. 33, pages 2863 to 2866 (1969).

The following controls were also employed:

| Control run | Compound |
|---|---|
| E | Acetone |
| F | 4-(3-phenyl-2-propenyl) phenol [PP] |
| G | None |
| H | None |

After exposure, the discs were removed from the water and oven-dried to a constant weight. X-ray techniques were used to determine the extent of teredine damage. By combining a visual examination of the X-ray prints and a count of the number of boring animals present, the specimen was rated according to the following scale: 0 = no apparent damage, 1 = light damage, 2 = moderate damage, and 3 = heavy damage. The results are summarized in the table below.

| Run | Agent | Amount of agent (%) | Damage |
|---|---|---|---|
| A | PC-2-OH-5-CH₃ | 3 | 0 |
| B | PC-2-OH-5-OCH₃ | 3 | 0 |
| C | PC-2-OCH₃-5-OCH₃ | 3 | 0 |
| D | 1:1 mixture of PC-20H-5-OCH₃:PP | 3 (per component) | 0 |
| Control run | | | |
| E | Acetone | — | 3.0 |
| F | PP | 3 | 3.0 |
| G | None | — | 3.0 |
| H | None | — | 3.0 |

EXAMPLE 3

Preservation of Pine under Field Conditions

Pine discs impregnated with the agents of the invention were prepared as described in Example 2.

The treated discs were exposed to natural borer populations in the Bay of Panama at Naos Island, Canal Zone, and in Manzanillo Bay, an arm of the Carribbean, at Coco Solo, Canal Zone, for a period of 3 months.

After exposure, the discs were recovered, cleaned of accumulated fouling (barnacles, tubeworms, encrusting bryozoa, etc.) and then treated as described in Example 2 to determine the extent of destruction.

Compounds used as preservatives were:

| Run | Compound |
|---|---|
| J | 4-(3-phenylpropenylidene)-2-hydroxy-5-methyl-2,5-cyclohexadieneone [PC-2-OH-5-CH₃] |
| K | 4-(3-phenylpropenylidene)-2-hydroxy-5-methoxy-2,5-cyclohexadieneone [PC-2-OH-5-OCH₃] |
| L | 1/1 mixture of PC-2-OH-5-OCH₃/4-(3-phenyl-2-propenyl) phenol [PP] |

The following controls were employed:

| Control run | Compound |
|---|---|
| M | Acetone |
| N | 4-(3-phenyl-2-propenyl)phenol [PP] |
| O | None |
| P | None |

The results are summarized in the table below.

| Run | Agent | Amount of agent (%) | Damage Naos Island | Damage Coco Solo |
|---|---|---|---|---|
| J | PC-2-OH-5-CH₃ | 3 | 1.4 | 0.3 |
| K | PC-2-OH-5-OCH₃ | 3 | 1.3 | 0.5 |
| L | 1:1 mixture of PC-2-OH-5-OCH₃:PP | 3 (per component) | 1.0 | 0.1 |
| Control run | | | | |
| M | Acetone | — | 3.0 | 3.0 |
| N | PP | 3 | 2.9 | 1.0 |
| O | None | — | 2.3 | 3.0 |
| P | None | — | 3.0 | 2.5 |

It should be noted that the table indicates that the treated wood exposed at Naos Island was damaged to a greater extent than the wood exposed at Coco Solo. However, the control wood at both sites was heavily damaged by teredine borers. The difference in the amount of damage at the two sites may be a consequence of different borer populations, since two oceans and two distinct marine environments are involved. In any event, the data do show a difference in the amount of damage sustained by treated wood as compared to that sustained by the controls, which were very heavily damaged.

It should also be noted that the sample discs were exposed for a period of only three months. However, since the size of the discs (¼ inch × 2 inches diameter) is extremely small in comparison to the expansiveness of the testing sites, the three-month exposure is considered quite severe.

Having thus described our invention, we claim:

1. A process for inhibiting the deterioration of wood due to attack by marine boring organisms, which comprises applying to the wood a compound of the structure

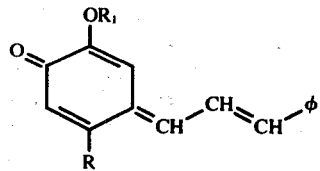

wherein R is lower alkyl and R₁ is selected from the group consisting of lower alkyl and hydrogen, in an amount sufficient to destroy the larvae of said marine boring organisms.

2. The process of claim 1 wherein the compound is 4-(3-phenylpropenylidene)-2-hydroxy-5-methyl-2,5-cyclohexadieneone.

3. The process of claim 1 wherein the compound is mixed in approximately equal proportions with 4-(3-phenyl-2-propenyl) phenol.

4. A process for inhibiting deterioration of wood subject to attack by marine borer larvae, which comprises applying to the wood a larvicidal amount of a compound of the structure

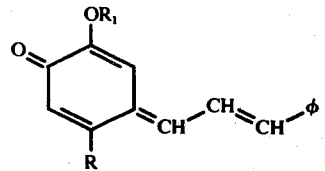

wherein R is lower alkyl and R₁ is selected from the group consisting of lower alkyl and hydrogen.

5. The process of claim 4 wherein the compound is 4-(3-phenylpropenylidene)-2-hydroxy-5-methyl-2,5-cyclohexadieneone.

6. The process of claim 4 wherein the compound is mixed in approximately equal proportions with 4-(3-phenylpropenyl) phenol.

7. A compound of the structure

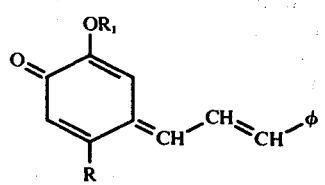

wherein R is lower alkyl and R₁ is selected from the group consisting of lower alkyl and hydrogen.

8. The compound of claim 7 wherein R is methyl and R₁ is hydrogen having the name 4-(3-phenylpropenylidene)-2-hydroxy-5-methyl-2,5-cyclohexadieneone.

* * * * *